(12) United States Patent
Takama et al.

(10) Patent No.: US 10,424,067 B2
(45) Date of Patent: Sep. 24, 2019

(54) IMAGE PROCESSING APPARATUS, IMAGE PROCESSING METHOD AND STORAGE MEDIUM

(71) Applicant: CANON KABUSHIKI KAISHA, Tokyo (JP)

(72) Inventors: Yasufumi Takama, Kawasaki (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/671,168

(22) Filed: Aug. 8, 2017

(65) Prior Publication Data

US 2017/0337694 A1    Nov. 23, 2017

Related U.S. Application Data

(63) Continuation of application No. 14/801,138, filed on Jul. 16, 2015, now Pat. No. 9,767,562.

(30) Foreign Application Priority Data

Jul. 24, 2014   (JP) .................................. 2014-151043

(51) Int. Cl.
*G06T 7/30* (2017.01)
*G06K 9/46* (2006.01)
*G06T 7/174* (2017.01)
*G16H 50/50* (2018.01)
(Continued)

(52) U.S. Cl.
CPC ................ *G06T 7/174* (2017.01); *G06T 7/33* (2017.01); *G16H 50/50* (2018.01); *G06T 7/0012* (2013.01)

(58) Field of Classification Search
CPC .......... G06T 7/0012; G06T 7/60; G06T 7/33; G06T 7/30; G06T 7/174; G06K 9/52; G06K 9/4671; G16H 50/50; G06F 19/00
See application file for complete search history.

(56) References Cited

U.S. PATENT DOCUMENTS

| 5,954,650 A | 9/1999 | Saito et al. |
| 6,560,354 B1 | 5/2003 | Maurer, Jr. et al. |
| 6,792,370 B2 | 9/2004 | Satoh et al. |

(Continued)

FOREIGN PATENT DOCUMENTS

| CN | 101783019 A | 7/2010 |
| JP | H10-137190 A | 5/1998 |
| JP | 2011-142974 A | 7/2011 |

OTHER PUBLICATIONS

Vujovic et al. "Establishing the Correspondence Between Control Points in Pairs of Mammographic Images." IEEE Transactions on Image Processing, vol. 6, No. 10, Oct. 1997 pp. 1388-1399 (Year: 1997).*

(Continued)

*Primary Examiner* — Jon Chang
(74) *Attorney, Agent, or Firm* — Venable LLP (57) ABSTRACT

An image processing apparatus comprises a corresponding point information obtaining unit configured to obtain corresponding point information input for alignment between images; a satisfaction degree obtaining unit configured to obtain a satisfaction degree of the corresponding point information based on the corresponding point information; and a presentation control unit configured to control presentation of information about the satisfaction degree.

27 Claims, 6 Drawing Sheets

(51) Int. Cl.
*G06T 7/33* (2017.01)
*G06T 7/00* (2017.01)

(56) References Cited

U.S. PATENT DOCUMENTS

| | | | |
|---|---|---|---|
| 6,993,450 B2 | 1/2006 | Takemoto et al. | |
| 7,092,109 B2 | 8/2006 | Satoh et al. | |
| 7,130,754 B2 | 10/2006 | Satoh et al. | |
| 7,446,768 B2 | 11/2008 | Satoh et al. | |
| 7,519,218 B2 | 4/2009 | Takemoto et al. | |
| 7,848,903 B2 | 12/2010 | Aratani et al. | |
| 8,416,987 B2 | 4/2013 | Tsuji | |
| 8,730,234 B2 | 5/2014 | Iizuka et al. | |
| 2003/0063788 A1* | 4/2003 | Boland | G06T 7/0012 382/132 |
| 2008/0317382 A1 | 12/2008 | Franz et al. | |
| 2010/0166261 A1 | 7/2010 | Tsuji | |
| 2014/0037161 A1 | 2/2014 | Rucker et al. | |
| 2014/0278232 A1 | 9/2014 | Miller et al. | |
| 2014/0348432 A1 | 11/2014 | Ishikawa et al. | |
| 2015/0049174 A1* | 2/2015 | Lee | H04N 13/221 348/50 |
| 2015/0070469 A1 | 3/2015 | Yoshibayashi et al. | |
| 2016/0042248 A1 | 2/2016 | Endo et al. | |

OTHER PUBLICATIONS

Fonseca et al. "Control Point Assessment for Image Registration." XII Brazilian Symposium on Computer Graphics and Image Processing, Aug. 6, 2002, 8 pages (Year: 2002).*

Sep. 4, 2017 Chinese Official Action in Chinese Application No. 201510434250.0.

* cited by examiner

| IMAGING PORTION 501 | IMAGING BODY POSTURE 502 | CASE INFORMATION 503 | | SATISFACTION DEGREE THRESHOLD 504 |
| --- | --- | --- | --- | --- |
| | | PATIENT AGE 5031 | BREAST SIZE 5032 | |
| BREAST | SAME | < 30 | SMALL | 0.2 |
| | | | LARGE | 0.3 |
| | | 30 - 50 | SMALL | 0.4 |
| | | | LARGE | 0.5 |
| | | > 50 | SMALL | 0.6 |
| | | | LARGE | 0.7 |
| | DIFFERENT | < 30 | SMALL | 0.2 |
| | | | LARGE | 0.6 |
| | | 30 - 50 | SMALL | 0.4 |
| | | | LARGE | 0.8 |
| | | 30 - 50 | SMALL | 0.6 |
| | | | LARGE | 1.0 |

IMAGE PROCESSING APPARATUS, IMAGE PROCESSING METHOD AND STORAGE MEDIUM

This application is a continuation of application Ser. No. 14/801,138 filed Jul. 16, 2015, U.S. Pat. No. 9,767,562 B2.

BACKGROUND OF THE INVENTION

Field of the Invention

The present invention relates to an image processing apparatus, an image processing method and a storage medium.

Description of the Related Art

In imaging diagnosis using a medical image (for example, a three-dimensional tomographic image representing information about the inside of an object), a doctor performs diagnosis while comparing images captured by a plurality of imaging apparatuses (modalities) in a plurality of body postures at different time with imaging parameters, and the like. Since, however, postures and shapes of an object differ between images, identification of a lesion region and comparison are difficult. Thus, alignment between a plurality of images is attempted. Conversion and deformation of the posture can be performed on one image to generate an image coincident with the other image. As a result, the doctor can readily perform identification of a lesion region and comparison between a plurality of images. Even in a field other than the medical field, in order to inspect the internal state of an object, a similar operation may be performed.

As a method of performing alignment between a plurality of images, Japanese Patent Laid-Open No. 2011-142974 discloses a method using manually provided corresponding point information between images. Also, Japanese Patent Laid-Open No. 2011-142974 discloses a technique of evaluating the quality of an alignment result based on the similarity between aligned images, and presenting a message to prompt correction according to the evaluation result.

In the technique disclosed in Japanese Patent Laid-Open No. 2011-142974, however, even if the quality of the alignment result is poor, the reason for this is uncertain. Consequently, the user cannot determine how to improve the alignment result, resulting in difficulty in improving the alignment accuracy.

SUMMARY OF THE INVENTION

The present invention has been made in consideration of the above problem, and provides a technique of improving the accuracy of alignment between images.

According to one aspect of the present invention, there is provided an image processing apparatus comprising: a corresponding point information obtaining unit configured to obtain corresponding point information input for alignment between images; a satisfaction degree obtaining unit configured to obtain a satisfaction degree of the corresponding point information based on the corresponding point information; and a presentation control unit configured to control presentation of information about the satisfaction degree.

According to one aspect of the present invention, there is provided an image processing apparatus comprising: a corresponding point information obtaining unit configured to obtain corresponding point information input for alignment between images; a reliability degree obtaining unit configured to obtain, as a distribution, reliability degrees of alignment at a plurality of points of interest on an image based on distances between each point of interest and respective corresponding points on the image; and a presentation control unit configured to present information indicating the distribution of the reliability degrees.

According to one aspect of the present invention, there is provided an image processing method comprising: a corresponding point information obtaining step of obtaining corresponding point information input for alignment between images; a satisfaction degree obtaining step of obtaining a satisfaction degree of the corresponding point information based on the corresponding point information; and a presentation control step of controlling presentation of information about the satisfaction degree.

According to one aspect of the present invention, there is provided an image processing method comprising: a corresponding point information obtaining step of obtaining corresponding point information input for alignment between images; a reliability degree obtaining step of obtaining, as a distribution, reliability degrees of alignment at a plurality of points of interest on an image based on distances between each point of interest and respective corresponding points on the image; and a presentation control step of presenting information indicating the distribution of the reliability degrees.

Further features of the present invention will become apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

An image processing apparatus according to this embodiment is an apparatus which performs alignment between a plurality of three-dimensional tomographic images, and calculates the satisfaction degree of corresponding point information between obtained images based on the reliability degree of alignment, and presents the calculation result to the user. The satisfaction degree is information indicating the number of corresponding points used for alignment in a three-dimensional tomographic image space. The reliability degree is information indicating the accuracy of alignment at arbitrary coordinates (a point of interest) in the three-dimensional tomographic image space. The image processing apparatus according to this embodiment will be described below.

<1. Arrangement of Image Processing Apparatus>

Figure 1:
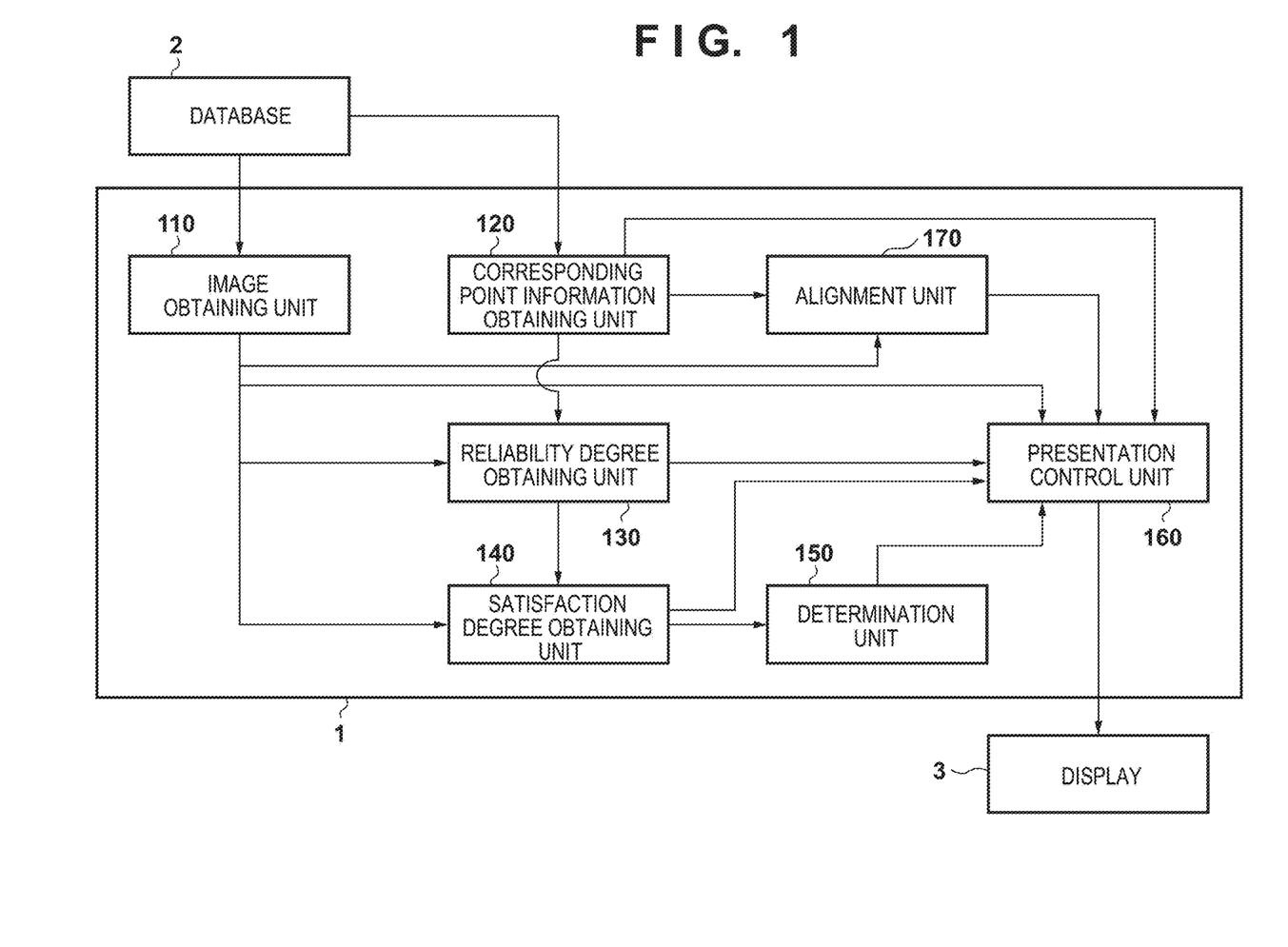
FIG. 1 is a block diagram showing an example of the arrangement of an image processing apparatus according to the first embodiment.

FIG. 1 is a block diagram showing an example of the arrangement of the image processing apparatus according to this embodiment. An image processing apparatus 1 includes an image obtaining unit 110, a corresponding point information obtaining unit 120, a reliability degree obtaining unit 130, a satisfaction degree obtaining unit 140, a determination unit 150, a presentation control unit 160, and an alignment unit 170. The image processing apparatus 1 is connected to a database 2 and a display 3. The database 2 stores the pieces of image information of three-dimensional tomographic images of an object captured by various modalities, and pieces of additional information.

The additional information of each image includes the size and resolution of the image, the type of modality, imaging information, and case information. The imaging information is information of an imaging portion and imaging body posture. The information of an imaging portion indicates, for example, a breast, liver, or brain. The information of an imaging body posture indicates, for example, a supine posture or prone posture. The case information includes, for example, patient information such as age and sex, information indicating the size of a target portion and a region to be aligned (for example, a region of an organ of interest), and information indicating a region of interest such as a lesion in an image space.

The image obtaining unit 110 obtains, from the database 2, the pieces of image information of the first and second images as three-dimensional tomographic images to be aligned, and pieces of additional information. The corresponding point information obtaining unit 120 obtains corresponding point information in the image coordinate system of each of the first and second images. Based on the information of corresponding points on the three-dimensional tomographic image of each of the first and second images, the reliability degree obtaining unit 130 obtains the reliability degree of alignment at a point of interest on the image. The reliability degree obtaining unit 130 generates a reliability degree map indicating the distribution of the reliability degrees.

The satisfaction degree obtaining unit 140 obtains the satisfaction degree of the corresponding point information based on the reliability degree obtained by the reliability degree obtaining unit 130. Based on the satisfaction degree of the corresponding point information obtained by the satisfaction degree obtaining unit 140, the determination unit 150 determines whether the corresponding point information obtained by the corresponding point information obtaining unit 120 is sufficiently satisfied for alignment between the images. The presentation control unit 160 controls to display, on the display 3, the satisfaction degree obtained by the satisfaction degree obtaining unit 140 and the determination result (the high/low satisfaction degree) obtained by the determination unit 150 as satisfaction information. The presentation control unit 160 also controls to display, on the display 3, the reliability degree map obtained by the reliability degree obtaining unit 130. The alignment unit 170 executes alignment processing between the images based on the corresponding point information obtained by the corresponding point information obtaining unit 120.

<2. Processing Sequence>

Figure 2:
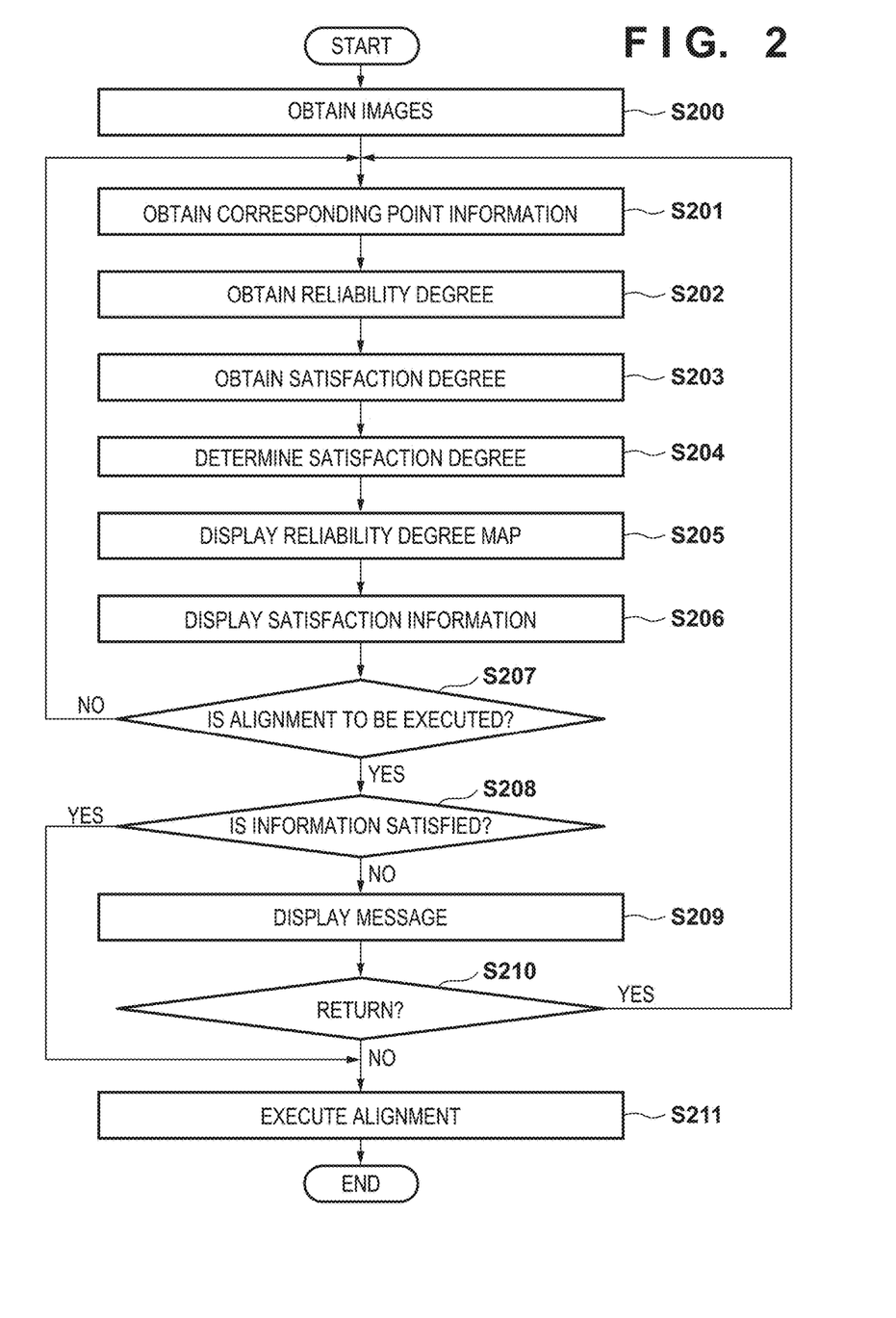
FIG. 2 is a flowchart illustrating a processing procedure executed by the image processing apparatus according to the first embodiment.

A processing procedure executed by the image processing apparatus 1 according to this embodiment will be described with reference to a flowchart shown in FIG. 2.

(Step S200; Obtaining of Images)

In step S200, the image obtaining unit 110 obtains, from the database 2, pieces of image information of the first and second images as three-dimensional tomographic images to be aligned, and pieces of additional information. The obtained pieces of image information are transmitted to the presentation control unit 160, and the tomographic images are displayed on the display 3. The obtained pieces of additional information are transmitted to the reliability degree obtaining unit 130 and satisfaction degree obtaining unit 140, as needed.

(Step S201; Obtaining of Corresponding Point Information)

In step S201, the corresponding point information obtaining unit 120 obtains corresponding point information in the image coordinate system of each of the first and second images. If the database 2 holds the corresponding point information, this information is obtained. If the user additionally inputs the corresponding point information, this information is obtained. The obtained corresponding point information is transmitted to the reliability degree obtaining unit 130, alignment unit 170, and presentation control unit 160.

Figure 3:
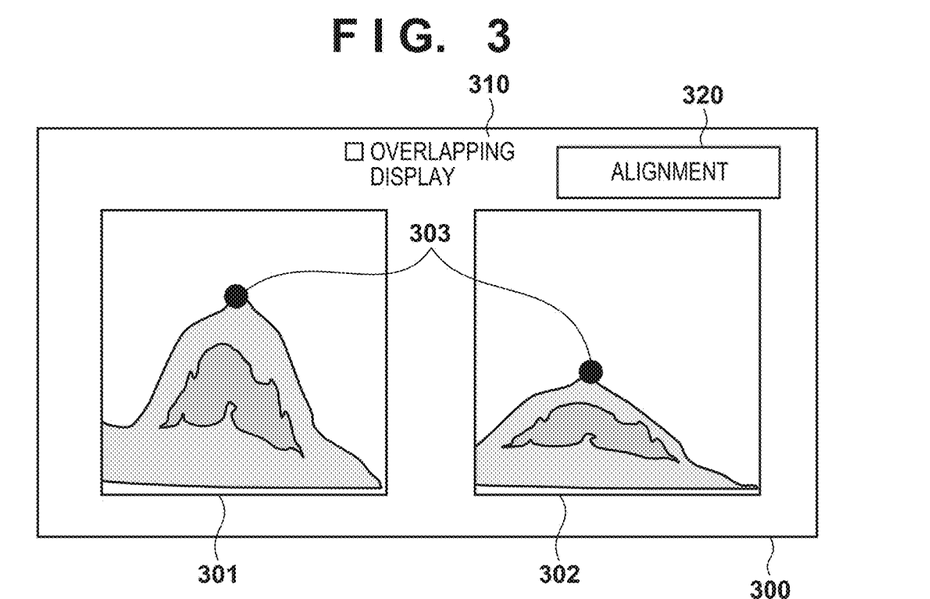
FIG. 3 is a schematic view showing a corresponding point input screen according to the first embodiment.

FIG. 3 is a schematic view showing a screen used by the user to input a corresponding point. The user inputs, as corresponding points 303, positions regarded as anatomically the same position on the respective images by clicking of a mouse or the like while comparing tomographic images 301 and 302 as three-dimensional tomographic images displayed on a corresponding point input screen 300 of the display 3. Here, tomographic images 301 is, for example, CT image or MRI image, and tomographic images 302 is, for example, ultrasound image. Note that the corresponding point information may be automatically obtained by image analysis processing. For example, feature points may be detected from the respective images, and corresponding points may be automatically obtained based on the similarity between image patterns. Also, the corresponding points automatically obtained by the image analysis processing may be set as candidates, and points manually corrected by the user may be set as the final corresponding point positions. Note that the functions of an overlapping display button 310 and alignment button 320 shown in FIG. 3 will be described later.

(Step S202; Obtaining of Reliability Degree)

In step S202, the reliability degree obtaining unit 130 calculates, based on the information of corresponding points on each three-dimensional tomographic image, the reliability degree of alignment at a predetermined point (each point of interest) on the image, and generates a reliability degree map indicating the distribution of the reliability degrees. The reliability degree map according to this embodiment is a volume image in which the voxel value of each point of interest on the three-dimensional image indicates the reliability degree of alignment at that point. In this embodiment, reliability degree map generation processing is executed for each of the first and second images. The generated reliability degree map is transmitted to the satisfaction degree obtaining unit 140 and presentation control unit 160.

A method of obtaining the reliability degree of alignment according to this embodiment will be described below. In alignment based on a corresponding point, alignment is generally more accurate at a point closer to the corresponding point, and less accurate at a point farther away from the corresponding point. In this embodiment, for each point (point of interest) on the image, the number of corresponding points of information obtained in a local region with reference to the position of the point of interest is derived. This is equivalent to deriving the local satisfaction degree of the corresponding points at the position. Assuming that the reliability degree of alignment is determined according to the local satisfaction degree of the corresponding points, the local satisfaction degree is defined as the reliability degree of alignment at the position. That is, the reliability degree of alignment at the point of interest is calculated based on the positional relationship between the point of interest and each corresponding point close to it. For example, the three-dimensional distances between the point of interest and the respective corresponding points are calculated, and the reliability degree of alignment at the position of the point of interest on the image is calculated based on the calculated three-dimensional distances. For example, the reliability degree is calculated based on a shortest distance d_min of the distances.

Figure 4:
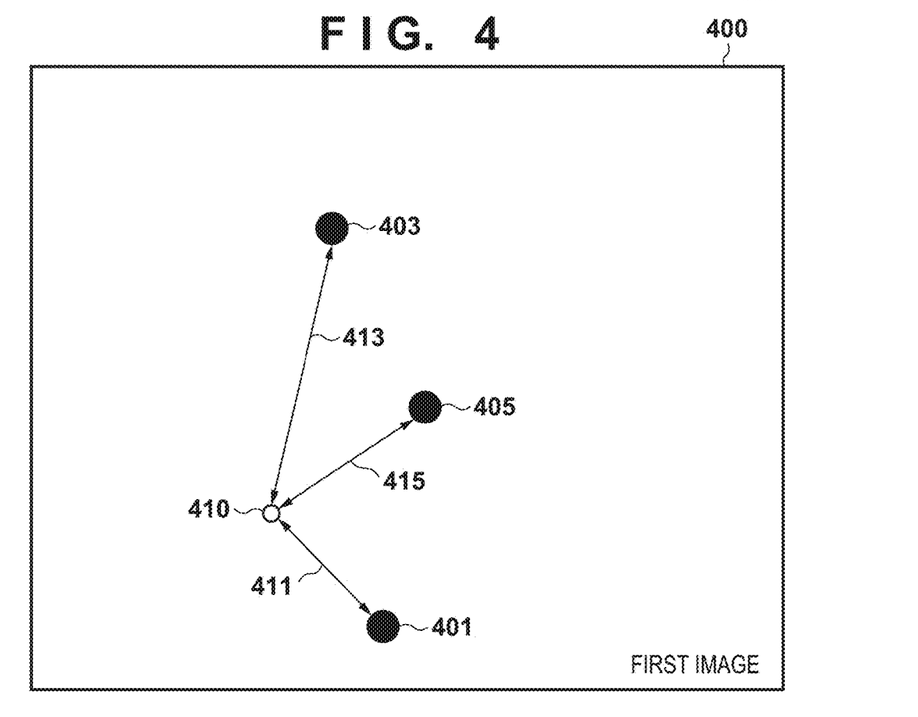
FIG. 4 is a schematic view showing the steps of processing of obtaining the reliability degree of alignment according to the first embodiment.

FIG. 4 is a schematic view showing a corresponding point 401 (a point on the side of a first image 400 of the pair of corresponding points set on the first image 400 and the second image (not shown) corresponding to it), corresponding points 403 and 405, and a point of interest 410 on the first image 400. These four points are not always on the same plane in the coordinate system of the first image 400.

The reliability degree obtaining unit 130 calculates three-dimensional distances (distances 411, 413, and 415) between the point of interest 410 and the corresponding points 401, 403, and 405. Based on the shortest distance d_min of these distances, the reliability degree at the point of interest 410 is calculated. For example, $1/(1+d\_min)$ is defined as the reliability degree, and calculated. At this time, if d_min=0, the reliability degree is 1.0. As the shortest distance d_min is longer, the reliability degree takes a value closer to 0. Alternatively, the reliability degree may be calculated to linearly decrease as the shortest distance d_min is longer. That is, the reliability degree may be defined to become highest (for example, 1.0) when the coordinates of the corresponding point coincide with the image coordinates, to decrease as the coordinates of the corresponding point are farther away from the image coordinates, and to become 0.0 when the coordinates of the corresponding point are away from the image coordinates by a given distance or more.

Note that the reliability degree obtaining method need not be based on the minimum value (shortest distance) of the three-dimensional distances from the point of interest to the respective corresponding points. For example, the reliability degree may be calculated based on the average value or median of the distances. Alternatively, the reliability degree may be calculated based on the Nth (N is a predetermined natural number) shortest distance. The reliability degree may be calculated based on the average value of upper N (N is a predetermined natural number) distances from the shortest distance. A combination (weighted average value) of a plurality of indices may be used. Furthermore, an arbitrary distance scale other than the Euclidean distance may be used as a distance. Also, the reliability degree may be calculated based on the number of corresponding points each at a distance equal to or shorter than a predetermined threshold. The reliability degree obtaining method may be changed according to the additional information (imaging portion information or the like) of the image obtained by the image obtaining unit 110 from the database 2 in step S200.

For example, if deformation is small like a liver, alignment is relatively accurate even away from a corresponding point, as compared with a case in which deformation is large like a breast. As for the liver, the reliability degree is linearly calculated so that the reliability degree of alignment gradually and constantly decreases in a direction away from the corresponding point. As for the breast, the reliability degree within a given range from the corresponding point is set to 1.0, and the reliability degree is inversely proportional to the distance outside the range. It is possible to calculate the reliability degree in consideration of the magnitude of deformation by changing the reliability degree obtaining method according to the imaging portion. As for the breast, the magnitude of deformation also changes depending on the patient age and breast size, and thus the reliability degree may be calculated in consideration of them.

Note that a region in which the reliability degree is calculated may be the entire image, or a region of interest such as an organ region of interest or a lesion. In the latter case, the information of the organ region or the region of interest obtained by the image obtaining unit 110 from the database 2 in step S200 is referred to. The organ region or lesion region is obtained using image threshold processing or an existing region extraction method. Alternatively, a region of interest on the image designated by the user is obtained. Then, each point in the region is set as a point of interest, and the reliability degree is calculated for each point of interest. This can omit calculation unnecessary for processing of the succeeding stage. Furthermore, the point of interest may be set at all voxels within the region or at every predetermined interval (for example, every sixth voxel). This can shorten the reliability degree calculation time.

(Step S203; Obtaining of Satisfaction Degree)

In step S203, the satisfaction degree obtaining unit 140 obtains the satisfaction degree of the corresponding point information based on the reliability degrees obtained in step S202. The obtained satisfaction degree is transmitted to the determination unit 150 and presentation control unit 160.

For example, the minimum value (the minimum value of the reliability degrees of the plurality of points of interest) of the calculated reliability degrees (that is, the two reliability degree maps) can be used as a satisfaction degree. Alternatively, the average value or median of the reliability degrees of the plurality of points of interest may be used. The Mth (M is a predetermined natural number) lowest reliability degree value may be used. The satisfaction degree may be calculated based on the average value of the upper M (M is a predetermined natural number) from the lowest reliability degree. Furthermore, the ratio of points of interest having the reliability degree equal to or higher than a predetermined threshold may be defined as the satisfaction degree, and calculated. The weighted average value of the reliability degrees according to a distance from the region of interest on the image may be used. At this time, a range in which calculation processing is performed may be the entire image, an organ region of interest, or a region of interest designated by the user. The reliability degree at a representative position (for example, a barycentric position) in the region of interest may be used as the satisfaction degree. The satisfaction degree may be calculated based on only one reliability degree map.

(Step S204; Determination of Satisfaction Degree)

In step S204, based on the satisfaction degree of the corresponding point information obtained in step S203, the determination unit 150 determines whether the corresponding point information obtained in step S201 is satisfied. More specifically, the determination unit 150 determines whether the satisfaction degree is high or low by comparing the obtained satisfaction degree with a threshold. The determination result is transmitted to the presentation control unit 160.

Figure 5:
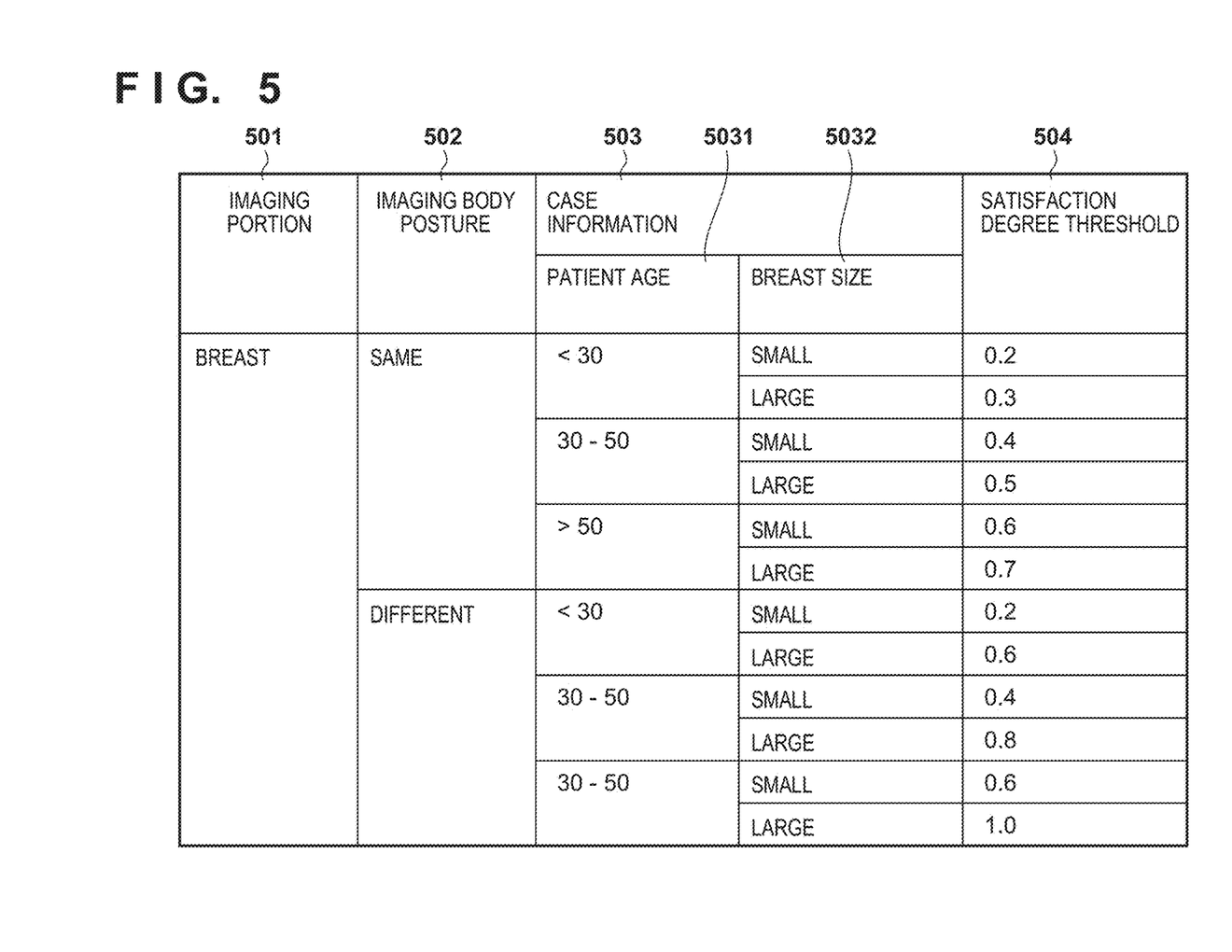
FIG. 5 is a table schematically showing an example of a determination table according to the first embodiment.

The determination unit 150 holds, as a determination table, a threshold set in advance for each set of an imaging portion, imaging body posture, and case information. FIG. 5 shows an example of the determination table. When the determination table is used, a satisfaction degree threshold 504 is set based on an imaging portion 501, imaging body posture 502, and case information 503 of an image. If, for example, deformation of the imaging portion 501 is large like a breast, it is necessary to set a high satisfaction degree, and thus the threshold 504 is set large. To the contrary, if deformation is small like a liver or brain, the satisfaction degree may be low, and thus the threshold 504 is set small.

Even if deformation is considered to be large like a breast, if the imaging body postures 502 of images to be compared are the same, the target shapes are almost equal to each other and thus the satisfaction degree threshold 504 may be relatively small. However, if the imaging body postures of the images are different from each other like a prone posture and supine posture, deformation is large, and the target shapes are largely different from each other. Thus, the threshold 504 is set large. The softness of the breast varies depending on the age. The threshold 504 may be changed depending on a patient age 5031 and breast size 5032 of the case information 503. As the age is younger, the breast is harder and deformation is smaller, and thus the threshold 504 is set smaller. As the age is older, the breast is softer and deformation is larger, and thus the threshold 504 is set larger. As the breast is smaller, deformation is smaller and thus the threshold 504 is set smaller. As the breast is larger, deformation is larger and thus the threshold 504 is set larger. As described above, based on the imaging portion 501, the imaging body posture 502, and the patient age 5031 and breast size 5032 of the case information 503, the determination unit 150 refers to the determination table to obtain the satisfaction degree threshold 504. That is, the satisfaction degree determination method is changed according to the additional information of the image.

Note that the result of determining whether the reliability degree at each position is high or low may be obtained by comparing each voxel value of the reliability degree map with the threshold, and a second reliability degree map having the values may be generated.

(Step S205; Display of Reliability Degree Map)

In step S205, the presentation control unit 160 controls to display, on the display 3, the reliability degree maps obtained in step S202.

Figure 6:
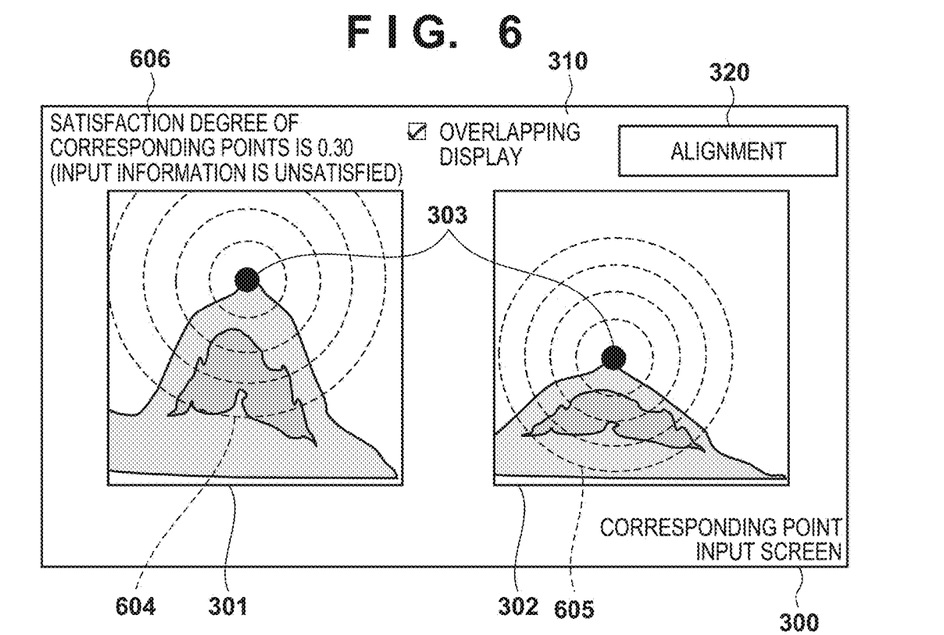
FIG. 6 is a schematic view showing overlapping display of a reliability degree map on a displayed tomographic image according to the first embodiment.
Figure 7:
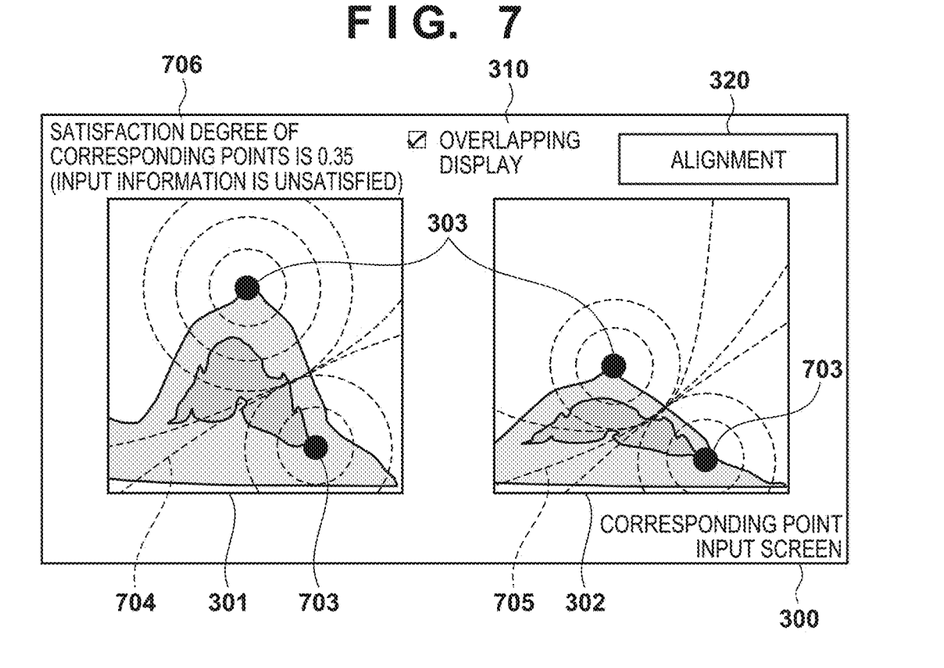
FIG. 7 is a schematic view showing a reliability degree map when a corresponding point is added according to the first embodiment.

FIGS. 6 and 7 are schematic views when reliability degree images 604 and 605 (704 and 705) are displayed to overlap the tomographic images 301 and 302 in the corresponding point input screen 300, respectively. The reliability degree images 604 and 605 (704 and 705) are tomographic images obtained by cutting the reliability degree maps obtained in step S202 along cross-sections corresponding to the tomographic images 301 and 302.

The luminance value of each image is a value obtained by converting the voxel value of the reliability degree map. For example, a grayscale reliability degree map is created by, for example, converting a reliability degree of 1.0 into a luminance value of 255 and a reliability degree of 0.0 into a luminance value of 0. A pseudo-color is assigned to this reliability degree map, and the reliability degree map is displayed as a pseudo-color map. As shown in FIG. 6, when one corresponding point is input, reliability degrees are distributed in a concentric spherical shape in the reliability degree map. In this case, in each of the reliability degree images 604 and 605, the corresponding point 303 is at the center of the concentric sphere, and the image is represented by pixel values indicating that a reliability degree closer to the corresponding point is higher and a reliability degree farther away from the corresponding point is lower. Furthermore, as shown in FIG. 7, when one corresponding point is added, reliability degrees are distributed in a concentric spherical shape by centering the corresponding point 303 and a corresponding point 703 like the reliability degree image 704 or 705.

Note that the reliability degree image may be displayed beside the tomographic image or displayed to overlap the tomographic image. The overlapping display can be controlled by, for example, turning on/off, by the user, the overlapping display button 310 displayed on the corresponding point input screen 300. When the overlapping display button 310 is OFF, the reliability degree image is set in a non-display state and only the tomographic image is displayed. When the overlapping display button 310 is ON, the reliability degree image and the tomographic image are displayed to overlap each other. By displaying the reliability degree image to overlap the tomographic image, the user can readily grasp, on the tomographic image, a region where a reliability degree is low, that is, a region where corresponding points are unsatisfied.

Note that if the second reliability degree map is generated in the processing of step S204, this information may be displayed to overlap the tomographic image. For example, red or the like may be semi-transparently displayed to overlap a voxel in which the reliability degree is equal to or lower than a threshold, so that the user can more explicitly confirm a portion having a low reliability degree. The user may be able to select a reliability degree map to be displayed by overlapping.

(Step S206; Display of Satisfaction Information)

In step S206, the presentation control unit 160 controls to display, as satisfaction information on the display 3, the satisfaction degree obtained in step S203 and the result of determining in step S204 whether the satisfaction degree is high or low.

Figure 8:
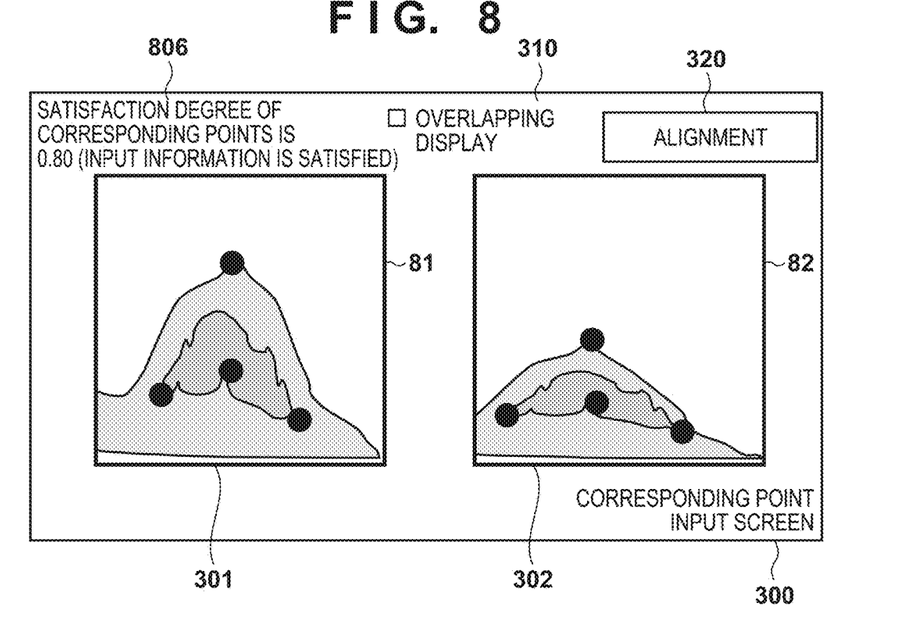
FIG. 8 is a schematic view showing a method of presenting that corresponding points are satisfied according to the first embodiment.

For example, as shown in FIG. 6, 7, or 8, the numerical value of the obtained satisfaction degree and information indicating whether corresponding points are satisfied are presented to the user as satisfaction information 606 (satisfaction information 706 or 806) on the corresponding point input screen 300. At this time, the threshold 504 used for the determination processing in step S204 may be displayed beside the satisfaction degree. The ratio (arrival ratio) of the satisfaction degree to the threshold may be displayed. Note that a satisfaction information presentation method is not limited to display of characters. For example, as shown in FIG. 8, when it is determined that the corresponding points are satisfied, a display mode of, for example, emphasizing and displaying outer frames 81 and 82 of the tomographic images 301 and 302 may be adopted. Satisfaction information may be presented by a sound (voice or beeper) or a vibration.

(Step S207; Alignment Execution Determination)

In step S207, the image processing apparatus 1 obtains an instruction about execution of alignment processing from the user, and branches the process according to the instruction. For example, it is determined whether the user has pressed the alignment button 320 shown in FIG. 3. If the image processing apparatus 1 obtains an alignment processing execution instruction, it advances the process to step S208. On the other hand, if the image processing apparatus 1 obtains no execution instruction, it returns the process to step S201 to accept an additional input of new corresponding point information.

The above processing allows the user to determine whether to continue the input of a corresponding point by referring to the displayed reliability degree map and satisfaction information. If the input of a corresponding point is continued, a region where the reliability degree is low is visualized. Thus, it is possible to efficiently improve the reliability degree by inputting a corresponding point to the region. Improvement in reliability degree can improve the satisfaction degree, and guide the user toward completion of the corresponding point input processing.

(Step S208; Satisfaction Determination)

In step S208, the image processing apparatus 1 branches the process according to whether the corresponding point information is satisfied or not. That is, if it is determined in step S208 that the corresponding point information is satisfied, the process advances to step S211; otherwise, the process advances to step S209.

(Step S209; Display of Message)

Figure 9:
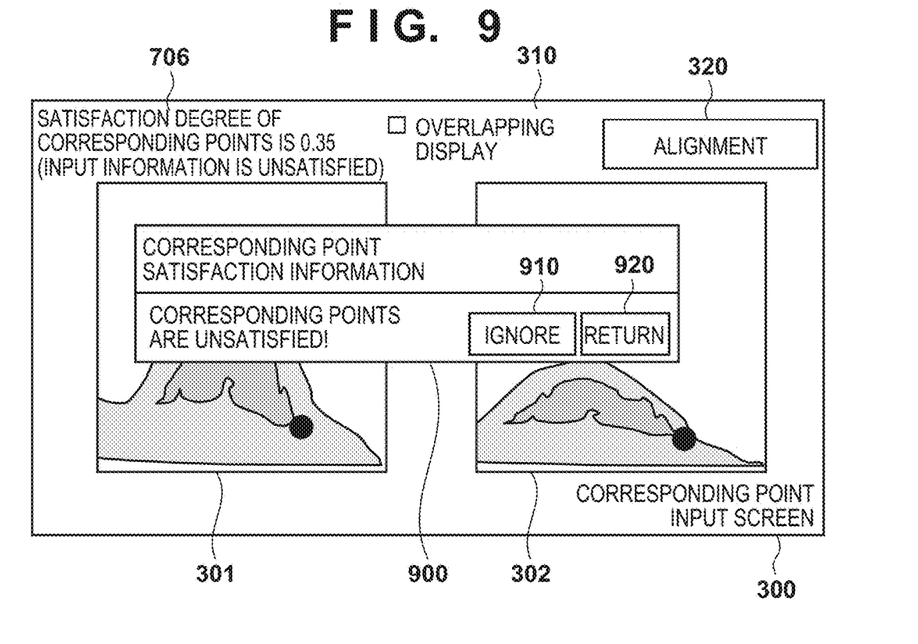
FIG. 9 is a schematic view showing a display example of warning that corresponding points are unsatisfied according to the first embodiment.

In step S209, the presentation control unit 160 controls to display, on the display 3, that the corresponding point information is not satisfied. For example, a warning message (notification window 900) shown in FIG. 9 is presented to the user. The user is prompted to instruct whether he/she accepts the warning to return to a corresponding point input operation or ignores the warning to execute alignment processing. More specifically, a GUI (for example, a denial button 910 ("ignore") and an affirmation button 920 ("return") in FIG. 9) for obtaining an instruction is displayed.

(Step S210; Determination of Whether to Return)

In step S210, the image processing apparatus 1 obtains a user instruction about whether to execute alignment processing, and branches the process according to the instruction. That is, if the image processing apparatus 1 obtains an instruction to accept the warning to return to a corresponding point input operation (the affirmation button 920 shown in FIG. 9 has been pressed), the process returns to step S201 to accept an additional input of new corresponding point information. On the other hand, if the image processing apparatus 1 obtains an instruction to ignore the warning to execute alignment processing (the denial button 910 shown in FIG. 9 has been pressed), the process advances to step S211.

(Step S211; Alignment)

In step S211, the alignment unit 170 executes alignment processing of the two images based on the obtained corresponding point information. The alignment unit 170 then generates a new image by performing coordinate transformation for the second image so that the second image coincides with the first image, and displays/saves the generated image. Note that alignment processing of images based on corresponding point information is well known and a detailed description thereof will be omitted. For example, any method of minimizing the distance between corresponding points after alignment, such as deformation alignment using rigid transformation estimation, affine transformation estimation, or FFD (Free-Form Deformation) can be used. Then, each process of the flowchart shown in FIG. 2 ends.

As described above, the image processing apparatus 1 according to this embodiment includes a corresponding point information obtaining unit 130 configured to obtain corresponding point information (corresponding points 303, 401, 403, 405, 703) input for alignment between images (tomographic images 301, 302, 400), a satisfaction degree obtaining unit 140 configured to obtain the satisfaction degree (satisfaction information 606, 706, and 806) of the corresponding point information based on the corresponding point information, and a presentation control unit 160 configured to control presentation of information (the numerical value of the obtained satisfaction degree such as satisfaction information 606, 706, or 806, and information indicating whether the information is satisfied) about the satisfaction degree.

Also, the image processing apparatus 1 according to this embodiment includes a corresponding point information obtaining unit 130 configured to obtain corresponding point information (corresponding points 303, 401, 403, 405, and 703) input for alignment between images (tomographic images 301, 302, 400), and a reliability degree obtaining unit configured to obtain, as a distribution, based on a distance 411, 413, or 415 between a point of interest 410 and each corresponding point 401, 403, or 405 on an image, the reliability degrees of alignment at a plurality of points of interest on the image, and a presentation control unit 160 configured to present information (reliability degree image 604, 605, 704, 705) indicating the distribution of the reliability degrees.

This allows the user to know satisfaction information of corresponding points (whether the corresponding points are satisfied) when performing alignment between a plurality of images. The user can refer to the information to determine whether to terminate the input operation of corresponding point information. Since it is possible to confirm the satisfaction degree before starting alignment processing, it is possible to save an unnecessary time to input corresponding point information again after the end of the processing. That is, it is possible to avoid alignment using unsatisfactory corresponding point information.

Furthermore, the user can confirm a region where the reliability degree is low by referring to the reliability degree map of alignment, and improve the reliability degree of alignment by adding a corresponding point to the region. As a result, it is possible to improve the accuracy of alignment between images.

Furthermore, when the result of determining the quality of the alignment result as described in Japanese Patent Laid-Open No. 2011-142974 indicates that the alignment result is incorrect, it can be determined whether there is a problem in the satisfaction degree of the corresponding points. If the corresponding points are satisfied but alignment is incorrect, it can be determined that there is an error in input corresponding point information.

(Modification 1-1)

In the processing of step S202, generation of a reliability degree map is not always indispensable. For example, a reliability degree at only one representative position (for example, a barycentric position) in the region of interest may be obtained. In this case, in step S205, no reliability degree map is displayed. In step S203, the obtained reliability degree is used as a satisfaction degree. This can largely reduce the calculation amount.

Second Embodiment

In the first embodiment, an example of obtaining a satisfaction degree based on the reliability degree of alignment has been explained. However, obtaining of the satisfaction degree need not always be based on the reliability degree of alignment. In this embodiment, an example of obtaining a satisfaction degree based on other information obtained from corresponding point information will be described. Furthermore, in this embodiment, an example of determining, based on an example of an input of corresponding point information in a similar past case, whether the satisfaction degree is high or low will be described.

<1. Arrangement of Image Processing Apparatus>

Components of an image processing apparatus according to this embodiment, which are different from those in the first embodiment, will be explained below. Note that the arrangements of an image processing apparatus 1, database 2, and display 3 according to this embodiment are the same as those in the first embodiment and a description thereof will be omitted. Assume that a record of performing alignment processing (input of corresponding point information) for a past case (a set of images) is saved as an example in the database 2 according to this embodiment, and additional information (an imaging portion, an imaging body posture, and case information) and corresponding point information of an image are stored in association with each other. Furthermore, no reliability degree obtaining unit 130 exists in the image processing apparatus 1 according to this embodiment, and corresponding point information obtained by a corresponding point information obtaining unit 120 is transmitted to a satisfaction degree obtaining unit 140.

<2. Processing Sequence>

The operations and processing procedure of the respective units of the image processing apparatus 1 according to this embodiment will be described with reference to a flowchart shown in FIG. 2. Note that in this embodiment, processes in steps S202 and S205 associated with obtaining and display of a reliability degree are not executed. Note that processes other than those in steps S203 and S204 are the same as in the first embodiment and a description thereof will be omitted.

(Step S203; Obtaining of Satisfaction Degree)

In step S203, the satisfaction degree obtaining unit 140 obtains the satisfaction degree of corresponding point information based on the corresponding point information obtained in step S201. In this embodiment, the number of obtained corresponding points is set as a satisfaction degree. The calculated satisfaction degree is transmitted to a determination unit 150 and a presentation control unit 160.

(Step S204; Determination of Satisfaction Degree)

In step S204, based on the satisfaction degree of the corresponding point information obtained in step S203, the determination unit 150 determines whether the corresponding point information obtained in step S201 is satisfied. The determination result is transmitted to the presentation control unit 160.

In this embodiment, a criterion for determining a satisfaction degree is set using a result of searching for a similar past case based on an imaging portion, an imaging body posture, and case information. To do this, the determination unit 150 first combines a past case (a set of images) similar to a case (that is, the first and second images) as an alignment target with an imaging portion and imaging body posture, and searches the database 2 based on a patient age and breast size as case information. Any existing method is used as a method of searching for a similar case. Then, the number of corresponding points associated with the most similar case (corresponding points input at the time of alignment of the case) is obtained, and set as a threshold, thereby determining whether the satisfaction degree is high or low.

As described above, the image processing apparatus according to this embodiment obtains a satisfaction degree based on the number of obtained corresponding points. This can save the reliability degree calculation time, and present satisfaction information at high speed. Furthermore, it is possible to determine a satisfaction degree based on the number of corresponding points of a case estimated to deform in the same way by determining a satisfaction degree based on the result of searching for a similar case.

(Modification 2-1)

A threshold for determining in step S204 whether the satisfaction degree is high or low may be provided by another method. For example, a threshold may be provided by using a determination table, similarly to the first embodiment, or by using a predetermined fixed value independently of additional information of the image.

According to the present invention, it is possible to improve the accuracy of alignment between images.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-151043, filed Jul. 24, 2014, which is hereby incorporated by reference wherein in its entirety.

What is claimed is:

1. An image processing apparatus comprising:
    a corresponding point information obtaining unit configured to obtain corresponding point information, which represents a plurality of pairs of points corresponding on two images, to perform an alignment between the two images;
    an alignment unit configured to perform alignment processing between the two images on the basis of the corresponding point information;
    a determining unit configured to determine whether the corresponding point information obtained by the corresponding point information obtaining unit is satisfied or not; and
    a display controlling unit configured to cause a display unit to display a first GUI to instruct whether the alignment unit performs the alignment processing or not,
    wherein the display controlling unit causes the display unit to display the first GUI, in a case that the determining unit determines that the corresponding point information is not satisfied, and
    wherein the alignment unit performs the alignment processing, in a case that, via the first GUI, a user instructs that the alignment unit performs the alignment processing.

2. The image processing apparatus according to claim 1, wherein the corresponding point information obtaining unit is configured to obtain the two images and to obtain the corresponding point information by an image analysis processing for the two images.

3. The image processing apparatus according to claim 1, wherein the display controlling unit causes the display unit to display a second GUI to instruct an additional pair of points corresponding on the two images, in a case that, via the first GUI, a user instructs that the alignment unit does not perform the alignment processing.

4. The image processing apparatus according to claim 3, wherein the determining unit is configured to determine whether the corresponding point information which represents the plurality of pairs of points and the additional pair of points corresponding on the two images is satisfied or not.

5. The image processing apparatus according to claim 1, wherein the determining unit determines whether the corresponding point information is satisfied or not, in a case that a user instructs that the alignment unit performs the alignment processing.

6. The image processing apparatus according to claim 1, wherein the alignment unit performs the alignment processing, in a case that the determining unit determines that the corresponding point information is satisfied.

7. The image processing apparatus according to claim 1, wherein the corresponding point information obtaining unit is configured to obtain the two images and to obtain the corresponding point information by an image analysis processing for the two images,
    wherein the determining unit is configured to determine whether the corresponding point information obtained by the image analysis processing is satisfied, and
    wherein the display controlling unit causes the display unit to display a second GUI to instruct an additional pair of points corresponding on the two images, in a case that, via the first GUI, a user instructs that the alignment unit does not perform the alignment processing.

8. The image processing apparatus according to claim 7, wherein the determining unit is configured to determine whether the corresponding point information which represents the plurality of pairs of points and the additional pair of points corresponding on the two images is satisfied or not.

9. The image processing apparatus according to claim 1, wherein each of the two images is a three-dimensional image.

10. The image processing apparatus according to claim 1, wherein each of the two images is a medical image.

11. The image processing apparatus according to claim 1, wherein the determining unit determines whether the corresponding point information obtained by the corresponding point information obtaining unit is satisfied or not in accordance with (a) a reliability degree of alignment and (b) a threshold.

12. An image processing method comprising:
    obtaining corresponding point information, which represents a plurality of pairs of points corresponding on two images, to perform an alignment processing between the two images;
    determining whether the corresponding point information is satisfied or not;
    displaying, on a display unit, a first GUI to instruct whether the alignment processing is performed or not, in a case that the corresponding point information is not satisfied; and
    performing the alignment processing, in a case that, via the first GUI, a user instructs that the alignment processing is performed.

13. The image processing method according to claim 12, wherein the corresponding point information is obtained by an image analysis processing for the two images.

14. The image processing method according to claim 12, wherein a second GUI to instruct an additional pair of points corresponding on the two images is displayed on the display unit, in a case that, via the first GUI, a user instructs that the alignment processing is not performed.

15. The image processing method according to claim 14, further comprising determining whether the corresponding point information which represents the plurality of pairs of points and the additional pair of points corresponding on the two images is satisfied or not.

16. The image processing method according to claim 12, wherein the determining whether the corresponding point information is satisfied or not is performed, in a case that a user instructs that the alignment processing is performed.

17. The image processing method according to claim 12, wherein the alignment processing is performed, in a case that the corresponding point information is satisfied.

18. The image processing method according to claim 12, wherein each of the two images is a three-dimensional image.

19. The image processing method according to claim 12, wherein each of the two images is a medical image.

20. A non-transitory computer-readable storage medium storing a computer program for causing a computer to execute an image processing method comprising:
    obtaining corresponding point information, which represents a plurality of pairs of points corresponding on two images, to perform an alignment processing between the two images;
    determining whether the corresponding point information is satisfied or not;
    displaying, on a display unit, a first GUI to instruct whether the alignment processing is performed or not, in a case that the corresponding point information is not satisfied; and performing the alignment processing, in a case that, via the first GUI, a user instructs that the alignment processing is performed.

21. An image processing apparatus comprising:
a corresponding point information obtaining unit configured to obtain corresponding point information, which represents a plurality of pairs of points corresponding on two images, to perform an alignment between the two images;
an alignment unit configured to perform alignment processing between the two images on the basis of the corresponding point information;
a determining unit configured to determine whether the corresponding point information obtained by the corresponding point information obtaining unit is satisfied or not; and
a display controlling unit configured to cause a display unit to display a GUI to instruct whether the alignment unit performs the alignment processing or not,
wherein the display controlling unit causes the display unit to display a warning information, in a case that the determining unit determines that the corresponding point information is not satisfied.

22. The image processing apparatus according to claim 21, wherein the alignment unit performs the alignment processing, in a case that, via the GUI, a user instructs that the alignment unit performs the alignment processing.

23. The image processing apparatus according to claim 21, wherein the warning information includes an information that the corresponding point information is not satisfied.

24. The image processing apparatus according to claim 21, wherein the display controlling unit causes the display unit to display a first icon to ignore the warning information to perform alignment processing, in the case that the determining unit determines that the corresponding point information is not satisfied.

25. The image processing apparatus according to claim 21, wherein the display controlling unit causes the display unit to display a second icon to accept an additional input of new corresponding point information, in a case that the determining unit determines that the corresponding point information is not satisfied.

26. An image processing method comprising:
obtaining corresponding point information, which represents a plurality of pairs of points corresponding on two images, to perform an alignment processing between the two images;
determining whether the corresponding point information is satisfied or not;
displaying, on a display unit, a GUI to instruct whether the alignment processing is performed or not; and
displaying a warning information, on the display unit, in a case that the corresponding point information is not satisfied.

27. A non-transitory computer-readable storage medium storing a computer program for causing a computer to execute an image processing method comprising:
obtaining corresponding point information, which represents a plurality of pairs of points corresponding on two images, to perform an alignment processing between the two images;
determining whether the corresponding point information is satisfied or not;
displaying, on a display unit, a GUI to instruct whether the alignment processing is performed or not; and
displaying a warning information, on the display unit, in a case that the corresponding point information is not satisfied.

* * * * *